United States Patent [19]
Iglesias

[11] 3,990,456
[45] Nov. 9, 1976

[54] ANTI-ARCING RESECTOSCOPE LOOP

[76] Inventor: Jose J. Iglesias, 1341 North Ave., Elizabeth, N.J. 07200

[22] Filed: Apr. 22, 1975

[21] Appl. No.: 571,020

[52] U.S. Cl. .......................................... 128/303.15
[51] Int. Cl.² ........................................ A61B 17/32
[58] Field of Search .................. 128/303.13–303.17

[56] References Cited
UNITED STATES PATENTS

| | | | |
|---|---|---|---|
| 2,448,741 | 9/1948 | Scott et al. | 128/303.15 |
| 3,294,085 | 12/1966 | Wallace | 128/303.15 |
| 3,752,159 | 8/1973 | Wappler | 128/303.15 |
| 3,835,842 | 9/1974 | Iglesias | 128/303.15 |
| 3,939,839 | 2/1976 | Curtiss | 128/303.15 |

Primary Examiner—Robert W. Michell
Assistant Examiner—Lee S. Cohen
Attorney, Agent, or Firm—Scrivener Parker Scrivener and Clarke

[57] ABSTRACT

A cutting loop assembly for a resectoscope, which is used in performing transurethral operations, has spaced arms comprising insulated electrically conductive wires extending from a stem and connected at their distal ends by a depending bare wire loop. The arms are extended in length at their distal ends sufficiently that arcing between the upper ends of the depending loop and the adjacent end of the metallic stem of the telescope which forms part of the resectoscope cannot take place at the current and voltage being used. The loop is also inclined from its upper ends to its bottom in a direction proximate to the resectoscope so that its bottom part will cooperate with the lower inner wall of the insulated beak of the sheath of the resectoscope as the cutting loop assembly is moved to rest position, in order to complete a resection which is being performed.

5 Claims, 2 Drawing Figures

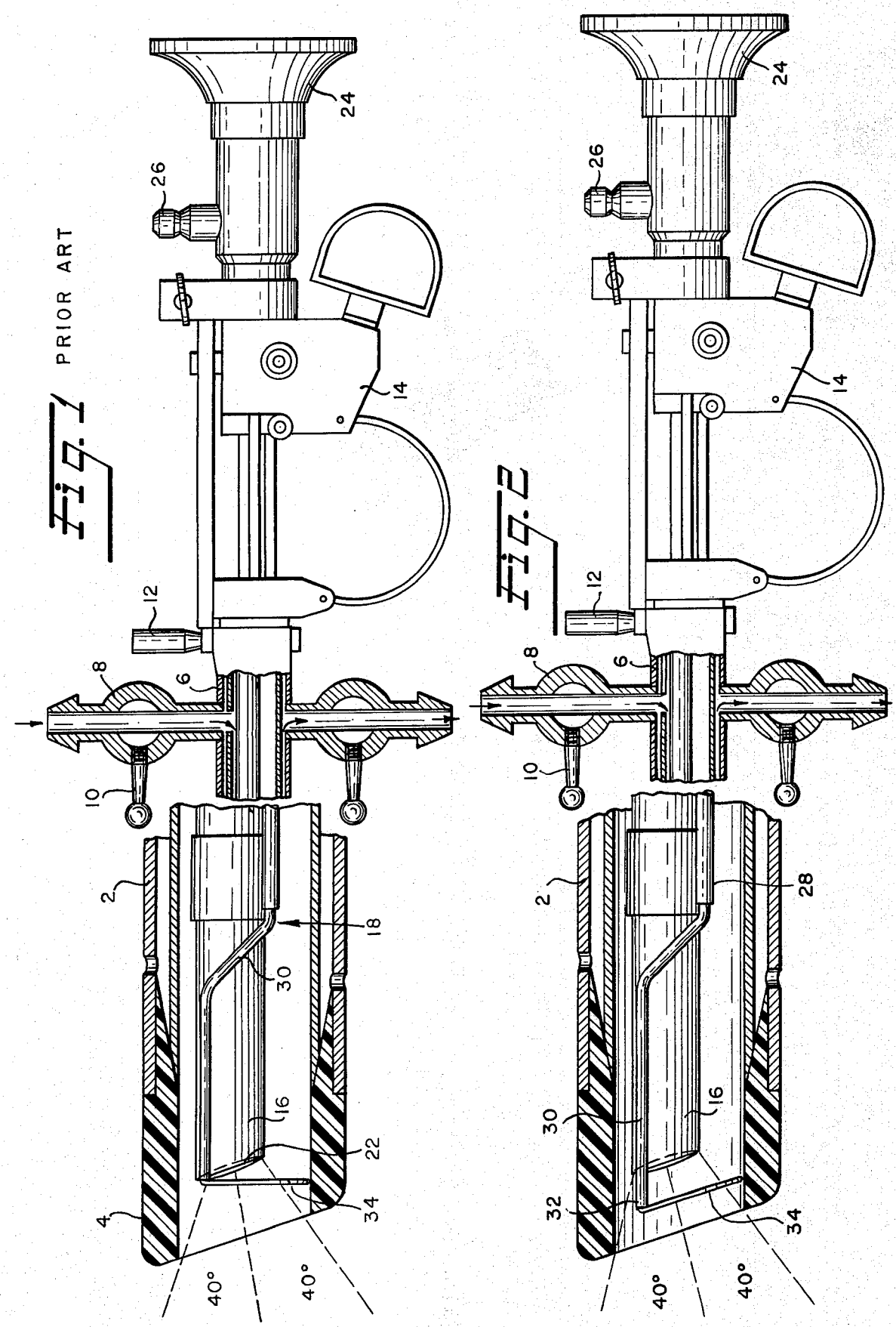

ANTI-ARCING RESECTOSCOPE LOOP

BACKGROUND OF THE INVENTION

A resectoscope for visually observing and performing transurethral resection of pathological changes at the prostate and bladder has a cutting loop assembly having spaced parallel insulated arms which at their distal ends support a depending bare wire loop which is activated by high frequency electrical current and which performs the cutting operation. Arcing between the distal ends of the arms or the upper ends of the depending loop and the adjacent distal end of the telescope tube often occurs when the cutting loop is moved to rest position, with consequent damage to the parts and adverse effect of the operative procedure.

A resectoscope having parts of conventional construction is disclosed in FIG. 1 as background for disclosure of the invention, and comprises the tubular sheath 2 which provides a passageway through the human urethra to the area of visual and operative interest, and which has at its distal end a beak 4 which is formed of an electrically insulating material such as a synthetic plastic and the shape of which is such that the side walls thereof recede in the proximate direction from the upper part of the distal end of the beak to the lower part. At its proximate end the sheath has a socket base 6 at which there is a tube 8 with stopcock 10 for the introduction of clear irrigating fluid, and a thumb screw 12 for attaching the sheath's socket to the working element 14 for reciprocally moving the cutting loop assembly and electrode between protracted and retracted positions longitudinally of the telescope stem in performing an operation. Within the sheath are the telescope stem 16 and the cutting loop electrode assembly 18.

The telescope has an objective lens 22 at its distal end and an ocular lens (not shown) and eyepiece 24 at its proximal end. Light conductors (not shown) extend through the telescope from an external connection 26 to the distal end for providing illumination. The field of vision at the operative field with the objective lens positioned as shown in FIG. 1 is illustrated by the broken lines shown in that figure and its shape is that of a truncated cone with the truncated surface at the objective lens.

The cutting loop electrode assembly 18 disclosed in FIGS. 1 and 2 comprises the elongated hollow stem 28 from the distal end of which there protrude two parallel arms 30, 32 which are insulated wires positioned on opposite sides of the telescope adjacent its distal end, and which are connected at their distal ends by a depending semi-circular bare wire cutting loop 34 which is activated by high frequency electrical energy to resect pathological tissues and coagulate bleeding vessels. The stem 28 and arms 30, 32 transmit electrical energy and the reciprocating movement of the working element 14 to the cutting loop 34.

FIG. 1 shows the bare wire cutting loop 34 in its conventional position extending downwardly at 90° to the spaced parallel insulated arms 30, 32 of the cutting loop assembly. Those arms are of such length that when the cutting loop assembly is retracted into the beak of the sheath during an operative procedure, as shown in FIG. 1, the bottom of the loop enters the beak in close proximity to the inner surface of the bottom wall of the beak, thus completing the resection of tissue, which is the object of the procedure.

Resectoscopes are now being provided with a telescope having the rod type lens which increases the total light and resolution at the operative field, and having a wider angle of vision than older types, because of which the distal end of the telescope must be very close to the beak of the sheath in order to prevent impairment of the field of vision by the end wall of the beak. As stated, the bare wire cutting loop must enter the insulated beak of the sheath in close proximity to its inner wall in order to complete a resection and this requirement, in conjunction with the distal extension of the telescope tube for visual reasons, has caused electrical arcing between the upper ends of the bare wire cutting loop and the distal end of the telescope, with consequent damage to the telescope, which is the most important and expensive part of the instrument, and adverse effect on the operative procedure. Among the methods suggested to correct this difficulty are (1) positioning the distal end of the telescope backward within the sheath beyond the position of optimum vision, (2) reducing the proximal movement of the cutting loop assembly in order to maintain the bare wire cutting loop at a safe distance from the telescope tube, and (3) extending the insulation of the spaced parallel arms of the cutting loop assembly over and beyond the junction of the arms and the depending loop. None of these has been satisfactory and none has prevented arcing, and the object of my present invention has been to prevent arcing while at the same time maintaining the increased illumination and field of vision provided by modern telescopes of resectoscopes, and insuring that the cutting loop will co-operate with the sheath in completing a resection.

SUMMARY OF THE INVENTION

The distal ends of the spaced insulated arms of the cutting loop assembly are extended in length so that the upper parts of the depending bare wire cutting loop are removed from the distal end of the metallic telescope stem when the assembly is in its most retracted position by a distance, which is preferably the minimum distance, necessary to prevent arcing between either bare wire of the loop and the adjacent end of the telescope stem at the current and voltage used, and the cutting loop is inclined from its upper end to its lower end toward the proximate end of the instrument at an angle which is such that the bottom part of the cutting loop will enter the beak of the sheath in close proximity to the beak in order to complete the resection which is being performed.

DESCRIPTION OF THE DRAWINGS

FIG. 1 is a side-elevational view of a resectoscope, being partially broken away, in section and enlarged to illustrate the prior art and its inherent problems, and FIG. 2 is similar in all respects to FIG. 1 but illustrates the parts modified by this invention.

DESCRIPTION OF THE INVENTION

In accordance with the invention, and as disclosed in FIG. 2, both of the spaced parallel arms 30, 32 of the cutting loop assembly are equally increased in length at their distal ends by such an amount that in the rest, or retracted, position of the cutting loop assembly, which is the position shown in both FIG. 1 and FIG. 2, the upper ends of the depending bare wire cutting loop 34 are spaced from the adjacent end of the telescope stem 16 by a distance, preferably the minimum distance, which is such that electrical arcing will not take place between the bare wire of the cutting loop and the adjacent parts of the telescope at the current and voltage being used. This distance may be 2.5 to 3.0 mm. for satisfactory results, this being the optimum minimum distance at presently used current and voltage.

In accordance with conventional practice, the insulation of the spaced arms 30, 32 is continued to the upper ends of the depending loop 34 but not onto the arms of the loop itself.

In further accordance with the invention the depending wire loop 34 is moved from its conventional position, as shown in FIG. 1, in which it depends from the spaced parallel arms 30, 32 at 90°, to a rearwardly inclined position, by which is meant that its bottom part is proximate to its upper ends and the plane of the loop is generally parallel to the objective lens of the telescope. In the preferred embodiment of the invention in which the upper ends of the loop 34 are 2.5 to 3.0 mm. distal to the nearest end of the telescope stem the loop is inclined rearwardly at approximately 30° to the vertical and at approximately 60° to the arms 30, 32. This rearward inclination of the cutting loop causes its lower part to enter the distal end of the sheath in close proximity and cutting relation to the lower part of the beak on movement of the cutting loop assembly to its retracted position in performing an operative procedure, thus insuring that the final step of a resection will take place by relative movement between the bottom part of the cutting loop and the inner wall of the lower part of the sheath 2. The rearward inclination of the loop, combined with the requirement that its lower edge part engage the lower inner wall of the beak, causes the loop to be larger than the conventional loop, as it forms the hypotenuse of a triangle rather than a side of the same triangle, which is the position and condition of the conventional loop.

The use of the means provided by the invention prevents arcing, permits final resection, and preserves all of the advantages of wide angle vision resulting from modern telescope construction.

I claim:

1. A resectoscope comprising a sheath, a telescope having an elongated metallic stem within said sheath and having proximal and distal ends, and a cutting loop within the sheath having a pair of spaced parallel insulated wire arms positioned respectively on opposite sides of the distal end part of the telescope stem, means for reciprocally moving said arms longitudinally of the telescope stem between protracted and retracted positions, said arms having distal ends positioned distal to the distal end of the telescope stem in the most retracted position, an arcuate bare wire loop connected at its ends to the distal ends of the arms and depending therefrom, the arms being of such length that when the cutting loop is in its most retracted position toward the telescope stem the upper ends of the loop are spaced distally from the distal end of the telescope stem by such a distance that arcing between the upper ends of the loop and the telescope stem will not take place at the current and voltage being used.

2. The resectoscope according to claim 1, in which the spacing between the upper ends of the loop and the distal end of the telescope stem is 2.5 to 3.0 millimeters.

3. The resectoscope according to claim 1, in which the loop is inclined in a direction toward the proximate end of the telescope stem from its upper ends to its bottom.

4. the resectoscope according to claim 3, in which the loop is inclined at approximately 60° to the spaced arms of the cutting loop assembly. The 5. As a new article of manufacture, a cutting loop for a resectoscope comprising an elongated stem having proximate and distal ends, a pair of insulated wire arms extending from the distal end of the stem having first upwardly extending and outwardly diverging sections terminating in distal ends and second parallel and spaced sections extending from the distal ends of the first sections and terminating in distal ends, and a depending bare wire loop connecting the distal ends of the second sections and being inclined in a rearward direction toward the proximate end of the stem from its upper ends to its bottom.

* * * * *